(12) United States Patent
Andréen

(10) Patent No.: US 11,027,055 B2
(45) Date of Patent: *Jun. 8, 2021

(54) IRRIGATION SYSTEM COMPRISING DUAL PUMPS

(71) Applicant: DENTSPLY IH AB, Mölndal (SE)

(72) Inventor: Erik Andréen, Gothenburg (SE)

(73) Assignee: DENTSPLY IH AB, Mölndal (SE)

( * ) Notice: Subject to any disclaimer, the term of this patent is extended or adjusted under 35 U.S.C. 154(b) by 84 days.

This patent is subject to a terminal disclaimer.

(21) Appl. No.: 16/262,540

(22) Filed: Jan. 30, 2019

(65) Prior Publication Data

US 2019/0160221 A1 May 30, 2019

Related U.S. Application Data

(63) Continuation of application No. 13/911,125, filed on Jun. 6, 2013, now Pat. No. 10,195,338.

(Continued)

(30) Foreign Application Priority Data

Jun. 7, 2012 (EP) ..................................... 12171174

(51) Int. Cl.
*A61M 3/02* (2006.01)

(52) U.S. Cl.
CPC ........ *A61M 3/0295* (2013.01); *A61M 3/0258* (2013.01); *A61M 3/0262* (2013.01); *A61M 3/0254* (2013.01); *A61M 2210/1067* (2013.01)

(58) Field of Classification Search
CPC .............. A61M 3/0262; A61M 3/0295; A61M 3/0254; A61M 3/0258; A61M 2210/1067
See application file for complete search history.

(56) References Cited

U.S. PATENT DOCUMENTS

| 6,106,494 A * | 8/2000 | Saravia ............... A61M 3/0258 |
| | | 604/151 |
| 2003/0073963 A1* | 4/2003 | Falconer ............. A61M 3/0262 |
| | | 604/328 |

(Continued)

FOREIGN PATENT DOCUMENTS

| GB | 238038 A | 8/1925 |
| RU | 2240141 C1 | 11/2004 |

(Continued)

OTHER PUBLICATIONS

European Office Action issued for Application No. 12171174.1, dated Oct. 21, 2015; 4 pages.

(Continued)

*Primary Examiner* — Tiffany Legette
*Assistant Examiner* — Tiffany Legette-Thompson
(74) *Attorney, Agent, or Firm* — Perkins Coie LLP

(57) ABSTRACT

An irrigation system is disclosed that can be uses in, for example, rectal irrigation. The system comprises a reservoir for an irrigating liquid and a probe for arrangement in a user. The probe includes an inflatable balloon for fixing the catheter in a body cavity. A first pump is provided to pump irrigation liquid from the reservoir to the probe, and a second pump is provided to pump a fluid to the balloon for inflation. A control unit controls the transfer of the irrigation liquid and the fluid, and includes a valve for releasing fluid from the balloon for deflation. Tubing provides fluid communication between the reservoir, control unit and probe. The control unit and the first and second pumps are further arranged as an integrated unitary component, and the manually operable balloon control element is arranged in the vicinity of the second pump.

23 Claims, 3 Drawing Sheets

Related U.S. Application Data

(60) Provisional application No. 61/656,673, filed on Jun. 7, 2012.

(56) References Cited

U.S. PATENT DOCUMENTS

| | | | |
|---|---|---|---|
| 2003/0120296 A1 | 6/2003 | Shturman et al. | |
| 2005/0148954 A1 | 7/2005 | Abell | |
| 2007/0073216 A1* | 3/2007 | McAuliffe | A61M 31/00 604/30 |
| 2009/0143745 A1* | 6/2009 | Langan | A61M 5/31 604/189 |
| 2010/0087792 A1 | 4/2010 | Nielsen et al. | |
| 2010/0324483 A1* | 12/2010 | Rozenberg | A61M 3/022 604/98.01 |

FOREIGN PATENT DOCUMENTS

| | | |
|---|---|---|
| WO | 03030968 A1 | 4/2003 |
| WO | 03030969 A1 | 4/2003 |
| WO | 2004006993 A1 | 1/2004 |
| WO | 2008087220 A1 | 7/2008 |
| WO | 2009080051 A1 | 7/2009 |
| WO | 2009092380 A1 | 7/2009 |
| WO | 2011023196 A1 | 3/2011 |
| WO | 2013160380 A1 | 10/2013 |

OTHER PUBLICATIONS

European Search Report, European Application No. 12171174.1, published Nov. 23, 2012; 6 pages.

International Search Report and Written Opinion for International Application No. PCT/EP2013/061576; dated: Jul. 26, 2013; 7 pages.

Russian Office Action issued for Application No. RU2014146513, dated Mar. 2, 2017, with translation; 16 pages.

\* cited by examiner

IRRIGATION SYSTEM COMPRISING DUAL PUMPS

CROSS-REFERENCE TO RELATED APPLICATION(S)

This patent application is a continuation of U.S. patent application Ser. No. 13/911,125, filed Jun. 6, 2013, which claims the benefit of and priority to EP Application Ser. No. 12171174.1, filed on Jun. 7, 2012 and U.S. Provisional Patent Application Ser. No. 61/656,673, filed on Jun. 7, 2012, which are herein incorporated by reference for all purposes.

TECHNICAL FIELD

The present invention relates to an irrigation system, comprising a reservoir for an irrigation liquid, a probe for arrangement in a user, and a control unit. The irrigation system is particularly intended for rectal irrigation, and is suitable for self-administration of an irrigation liquid.

BACKGROUND

The present invention relates to an irrigation device. Administrating an irrigation liquid is a common medical procedure whereby liquid is injected into a bodily cavity, such as into the rectum and lower intestine of a patient in order to induce bowel movement. The need for such a procedure typically arises in patients suffering from certain physical ailments in which voluntary bowel control is impaired or when the bowel needs to be cleaned before e.g. a coloscopy or a surgical operation. To this end, irrigation systems may be used e.g. by people suffering from spinal cord injuries, spina bifida or multiple sclerosis. For such users, irrigation may improve quality of life by preventing constipation, reducing time spent for bowel emptying procedures, reducing fecal incontinence, and by increasing independency in general.

Irrigation is nowadays often performed outside medical attendance premises, such as in the patient's home, and is also often performed by the patient himself, i.e. by self-administration. Hereby, the patient need to do multiple tasks at the same time, or immediately following on each other, such as inserting the probe in a correct position, adequately fixating the probe in the bodily cavity, enabling the liquid to be discharged for irrigation and discharge a correct dose of irrigation liquid, and removing the probe after use. Further, many of the users of irrigation systems have reduced dexterity, which makes the operation even more cumbersome.

It is further of importance that the irrigation system is of a limited size, and portable. Portability of the irrigation system is important to disabled persons who are not hospitalised or bed-ridden if they are to live as normal a life as possible. This is particularly important if they travel away from their home, for instance, to someone else's home or if they stay in a hotel. In this situation, they need to be able to deal with their bowel function easily.

Various irrigation systems are known in the art, such as is disclosed in WO 2008/087220, WO 2009/092380, WO 03/030969, WO 2011/023196 and WO 03/030968. However, despite the attempts to make these devices user friendly, all of these irrigation devices are still relatively complicated to use, especially for self-administration of the irrigation liquid, and also, most of these known devices are made of many different components and are relatively costly to produce.

There is therefore a need for an irrigation device which can be used safely, easily and conveniently for self-administration of the irrigation liquid, and which can be produced in a cost-efficient way.

SUMMARY OF CERTAIN EMBODIMENTS

In view of the above mentioned need, a general object of the present invention is to provide an irrigation system which alleviates the above-discussed problems of the prior art, and at least partly fulfils the above-discussed needs.

This and other objects are achieved with an irrigation system according to the appended claims.

According to the invention, there is provided an irrigation system comprising:
- a reservoir for an irrigating liquid;
- a probe for arrangement in a user, wherein said probe comprises an inflatable balloon for fixing the catheter in a body cavity;
- a first pump for directly or indirectly pumping irrigation liquid from the reservoir to the probe;
- a second pump for pumping a fluid to the balloon for inflation;
- a control unit for controlling the transfer of said irrigation liquid and said fluid, wherein said control unit further comprises a valve for releasing fluid from the balloon for deflation, said valve being provided with a manually operable balloon control element, and preferably a control button; and
- tubing providing fluid communication between said reservoir, control unit and probe;
- wherein said control unit and said first and second pumps are arranged as an integrated unitary component, and wherein said manually operable balloon control element is arranged in the vicinity of the second pump.

The irrigation system of the present invention comprises relatively few and uncomplicated components, which makes the irrigation system relatively easy and cost-efficient to produce. Further, the irrigation system lends itself well for automated or semi-automated manufacturing.

Further, the provision of the integrated control unit makes the irrigation system safe and easy to use, also for persons with reduced dexterity. This also makes the irrigation system highly suitable for self-administration of the irrigation liquid. The provision of the first and second pump together in the control unit makes it easy to access the pumps with one hand only, and to switch between the pumps. The provision of separate pumps for discharge of the irrigation liquid and for filling of the balloon, respectively, also alleviates the risk that the pumps are used erroneously, e.g. by further filling the balloon when a discharge of irrigation liquid is intended. Still further, the provision of a valve for releasing fluid from the balloon for deflation ensures that the balloon can be easily deflated after irrigation, and also that the filling level of the balloon can be precisely controlled, which makes it possible to adjust and optimize the filling level of the balloon during initial inflation, when the probe is fixed in the bodily cavity, or during irrigation. The arrangement of the manually operable balloon control element in the vicinity of the second pump is particularly advantageous, since it enables quick switching between inflation and deflation. By this arrangement, it is e.g. possible to operate the balloon control element with one finger, e.g. the thumb, and to operate the pump with the rest of the fingers. Hereby, the pump and the valve can be operated more or less simultaneously, which provides a very convenient and precise controllability of the filling level of the balloon.

When air is used as a balloon filling fluid, the valve for releasing fluid from the balloon may open up to a vent channel. The valve is in this embodiment closed by default, and opened up whenever the balloon filling fluid is to be released.

Preferably, at least one of the first and second pump is a manually operable pump, such as a bulb or a bellow pump. A manually operable pump is very cost-efficient, which lowers the overall costs of the product. Further, a manually operable pump provides a very precise controllability for the user. In particular, it is preferred that at least the second pump, i.e. the pump used for pumping fluid to the balloon for inflation, is a manually operable pump, since a very limited fluid volume is needed for adequate inflation of the balloon, and since it is of importance that the balloon is inflated with precision. Too low inflation may result in a too weak fixation, which may result in the probe falling out during irrigation. Too high inflation may be painful and even potentially harmful to the user.

Preferably, the manually operable pump is a bulb pump, comprising an inlet provided with a one-way valve, allowing a fluid to enter but not exit the pump, a pumping compartment and an outlet, provided with a one-way valve, allowing a fluid to exit but not enter the pump. The pumping compartment is made of a resilient, squeezable material, which retains it shape when unloaded. By squeezing the pumping compartment, the fluid is pumped out through the outlet, and when the squeezing is relieved, the pumping compartment retains its original shape, thereby sucking in fluid through the inlet.

For inflation of the balloon, any fluid may be used. For example, it is possible to connect the pump to the reservoir, and use irrigation liquid for filling of the balloon. It is also possible to provide a separate supply of another fluid, liquid or gas, for filling of the balloon. However, preferably ambient air is used for inflation of the balloon.

When air is used to fill the balloon, the valve may be a vent, discharging air out from the system for deflation. If e.g. irrigation liquid is used, the valve may instead release the irrigation liquid back to the reservoir or into the probe for discharge during irrigation. However, it is also possible to release the fluid from the balloon into a drain compartment or the like.

In one embodiment, both the first and second pumps are manually operable pumps, such as bulb or bellow pumps. Preferably, both pumps are of the same type, and preferably bulb pumps.

Preferably, the control unit further comprises a reservoir control valve for releasing pressure from the reservoir, said valve being provided with a manually operable reservoir control element, and preferably a control button. Hereby, a possible overpressure in the reservoir can easily be released after irrigation, and prior to removal of the probe from the patient. This makes removal of the probe more comfortable, and also reduces the risk of spillage. Preferably, the manually operable reservoir control element is arranged in the vicinity of the first pump, i.e. the pump used for directly or indirectly pumping irrigation liquid from the reservoir to the probe. Hereby, switching between the pump and the control element becomes easy. By this arrangement, it is e.g. possible to operate the control element with one finger, e.g. the thumb, and to operate the pump with the rest of the fingers. Hereby, the pump and the valve can be operated more or less simultaneously, which provides a very convenient and precise controllability.

The tubing preferably comprises a first tube connecting the first pump and the reservoir, a second tube connecting the reservoir and the probe, and a third tube connecting the second pump and the probe.

Preferably, the first pump and second pump are arranged to be visibly discernible from each other, and preferably by having at least one of different shapes and different colours. For example, the pump used for inflation of the balloon may be of a colour resembling air, such as grey or light blue, whereas the pump used for irrigation may be of a colour resembling water, such as deep blue. Additionally or alternatively, the pump used for inflation of the balloon may be slimmer or smaller than the pump used for irrigation. Hereby, accidental use of one pump when the other pump is intended is avoided.

As an alternative to having manually operated pumps, it is possible to use powered pumps, such as electrically or pneumatically operated pumps. Such powered pump may be used as the first pump, as the second pump or as both the first and second pumps.

In case one or more powered pumps are used, the control unit further preferably comprises a pump control element for activation of the powered pump, and preferably a control button.

The first pump may be arranged to pump irrigation liquid from the reservoir to the probe directly or indirectly. By direct pumping is here meant that the pumping is made directly on the irrigation fluid. Such a pump may e.g. be arranged in-line in a conduit leading from the reservoir to the probe. By indirect pumping is here meant that the pumping is made on a different fluid, such as air, which when pumped exerts a pressure to the irrigation fluid, whereby the irrigation fluid is also pumped. For example, the first pump is arranged to pump a gas, and preferably air, into the reservoir to create a pressure in the reservoir to displace the irrigation liquid therefrom and feed it to the probe.

The control unit preferably comprises at least three corners, wherein the first pump is arranged at a first corner and the second pump is arranged at a second corner. Even more preferably, the control unit comprises at least four corners, wherein tubing connecting the reservoir to the control unit is arranged at a third corner, and tubing connecting the control unit to the probe is arranged at a fourth corner. Such an arrangement provides a very convenient control unit to hold and manoeuvre. It is also preferred that the control unit has a planar shape, with tubing extending therethrough. However, many other shapes, such as curved or cylindrical shapes, are also feasible.

According to another aspect of the present invention, there is provided a use of the irrigation device as discussed above for rectal irrigation.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein.

DETAILED DESCRIPTION

Figure 1:
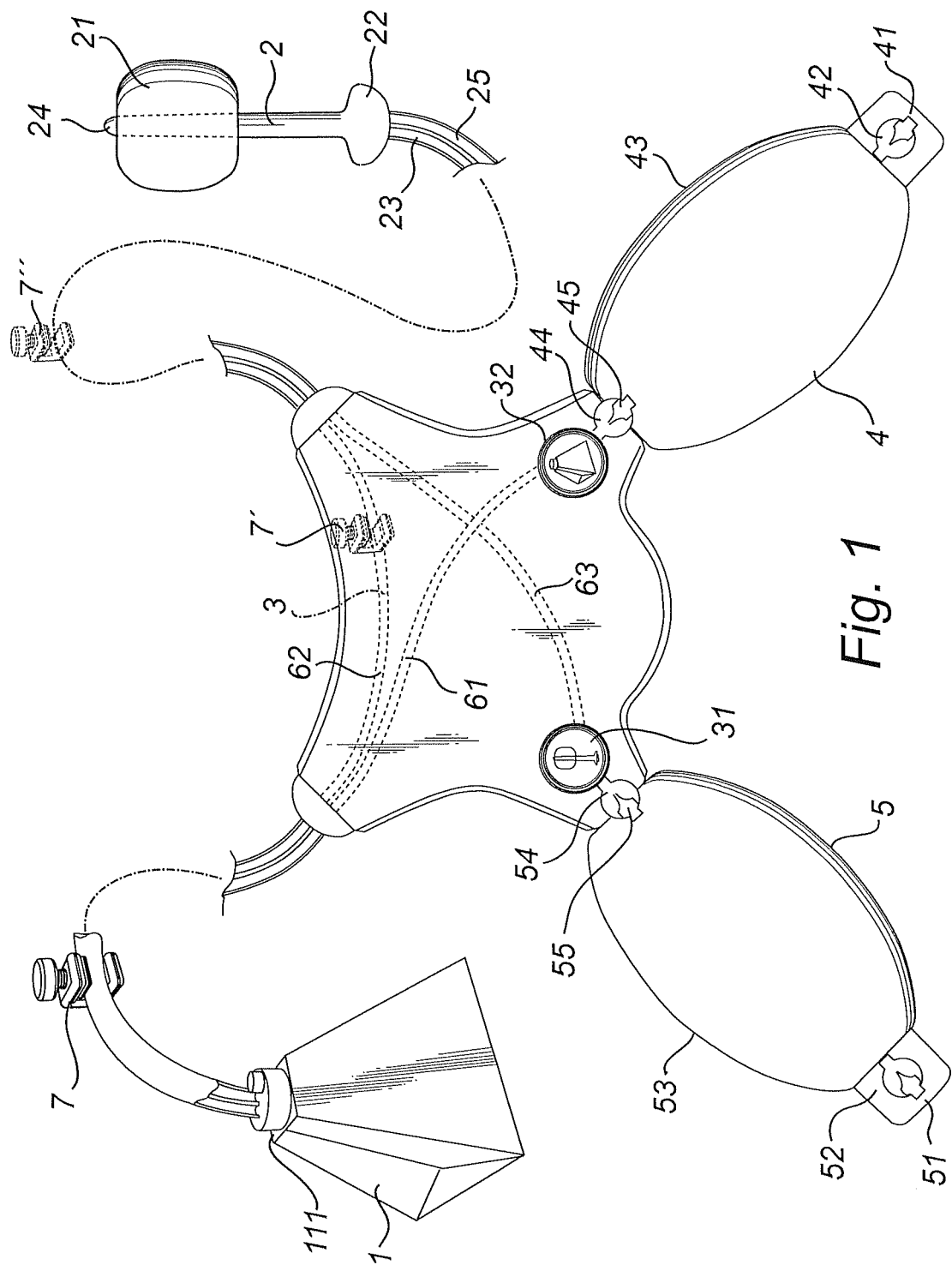
FIG. 1 is schematic overview of an irrigation system according to a first embodiment of the invention.

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout.

FIG. 1 discloses an irrigation system according to a first exemplary embodiment, comprising a reservoir 1 for an irrigating liquid, a probe 2 for arrangement in a user, and a control unit 3.

The reservoir may be realized in various ways. For example, the reservoir may be formed by a rigid, semi-rigid or flexible material. In case a semi-rigid or flexible material is used, the reservoir may be collapsible or foldable, to make the irrigation system more compact prior to use. The reservoir is provided with an opening, closed by a lid 11, for filling of the reservoir. Tubing connecting the reservoir to the rest of the irrigation system may be provided through the lid 11, or through other access points on the reservoir.

In order to render the irrigation system as portable as possible, the container preferably has a capacity of less than 5 litres, more preferred less than 3 litres and most preferred less than 2 litres. If however the system is to be used for repeated irrigation, a larger capacity container may be necessary.

The reservoir may comprise an overpressure release valve, to release pressure over a predetermined maximum pressure to be allowed.

The probe 2 is provided with an insertable balloon 21 for fixing the catheter in a body cavity. Further, the probe may be provided with a rearward enlarged part 22, providing an abutment to hinder too deep insertion. The probe is provided with two lumens—one lumen 23 for transfer of irrigation liquid through the probe, for discharge at the forward end 24, and one lumen 25 for inflation and deflation of the balloon.

The control unit is here realized as a plate, comprising at least three or four corners and preferably slightly curved sides, in order to provide good ergonomic handling of the control unit. One corner is connected to a first pump 4, for directly or indirectly pumping irrigation liquid from the reservoir to the probe. A second corner is connected to a second pump 5 for pumping a fluid to the balloon for inflation. A third and possibly a fourth corner may comprise tubings leading to the reservoir and the probe. The control unit and the first and second pumps are arranged as an integrated unitary component.

The control unit is further provided with a valve for releasing fluid from the balloon for deflation, and provided with a manually operable balloon control element 31. The control element is preferably realized as a depressible control button. The control element 31 is arranged in the vicinity of the second pump 5. Preferably, the control element is arranged within 5 cm from the pump.

In this embodiment, the first and second pumps are manually operable pump. However, other types of pumps are also feasible. In the shown example, the manually operable pumps are bulb pumps, comprising inlets 41, 51, each provided with a one-way valve 42, 52, allowing a fluid to enter but not exit the pump. Further, the pumps comprise pumping compartments 43, 53 and outlets 44, 54, provided with one-way valves 45, 55, allowing a fluid to exit but not enter the pump. The pumping compartment is made of a resilient, squeezable material, which retains its shape when unloaded. By squeezing the pumping compartment, the fluid is pumped out through the outlet, and when the squeezing is relieved, the pumping compartment retains its original shape, thereby sucking in fluid through the inlet.

In the illustrative example, the pumps are used to pump air. Thus, the second pump 5 pumps air into the balloon 21 for inflation, and the air is releasable through the valve 31. The first pump 4 is arranged to pump air into the reservoir, thereby creating an overpressure in the reservoir which pumps irrigation liquid out from the reservoir. To release pressure from the reservoir, the control unit further comprises a reservoir control valve for releasing pressure from the reservoir. The valve is provided with a manually operable reservoir control element 32, here realized as a control button. Hereby, a possible overpressure in the reservoir can easily be released after irrigation, and prior to removal of the probe from the patient. This makes removal of the probe more comfortable, and also reduces the risk of spillage. Preferably, the manually operable reservoir control element 32 is arranged in the vicinity of the first pump. Preferably, the control element 32 is arranged within 5 cm from the first pump.

In this embodiment, the tubing connecting the reservoir, control unit and probe comprises a first tube 61 connecting the first pump and the reservoir, a second tube 62 connecting the reservoir and the probe, and a third tube 63 connecting the second pump and the probe.

Preferred materials for the bulb pumps and the balloon can be any suitable material e.g. such as PVC, latex, TPE or PU. However, other materials providing similar properties can likewise be used.

As an alternative to having manually operated pumps, it is possible to use powered pumps, such as electrically or pneumatically operated pumps. Such powered pump may be used as the first pump, as the second pump or as both the first and second pumps.

A manually operable valve 7 may be provided for closing the fluid communication between the reservoir 1 and the probe 2. This may e.g. be used for closing this communication path during filling of the reservoir, during the initial preparations prior to irrigation, after the irrigation has been completed, etc. In the illustrative example, a clamp is used as the valve 7. However, as would be appreciated by the skilled addressee, many other types of manually operable valves are feasible. Further, in the illustrative example, the manually operable valve 7 is arranged on the tube extending between the reservoir and the control unit. However, additionally or alternatively, a manually operable valve 7' may be arranged on the control unit, and/or a manually operable valve 7" may be arranged on the tube extending between the control unit and the probe. Thus, the manually operable valve may be arranged anywhere along the fluid communication path between the reservoir and the probe, and also on multiple locations along said path.

Figure 2:
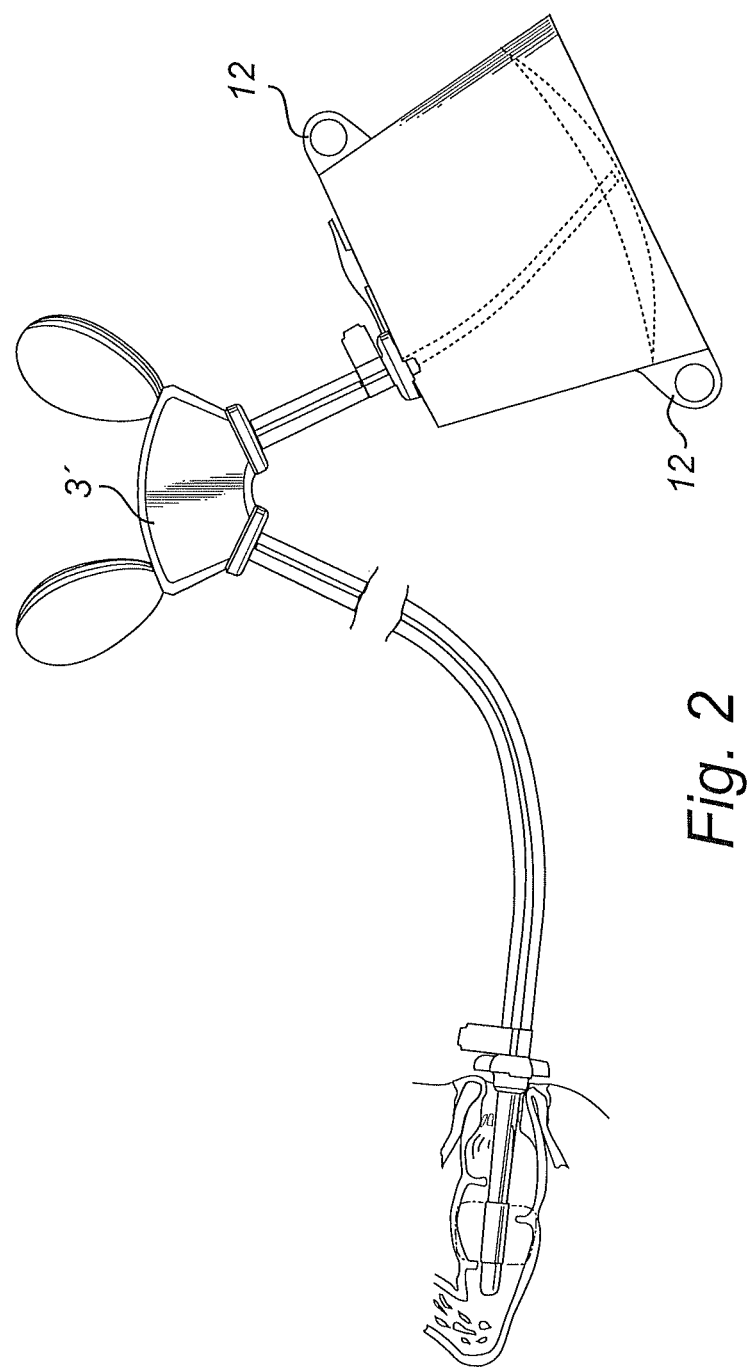
FIG. 2 is a schematic overview of an irrigation system according to a second embodiment of the invention.

The second embodiment, illustrated in FIG. 2, resembles the above-described first embodiment. However, here the control unit 3' has been provided with a different shape. Further, the reservoir has been provided with hangers 12, such as tabs with holes therein, to enable the reservoir to be arranged on hooks or the like. The probe is here illustrated in a state where it is inserted in an anal opening.

Figure 3:
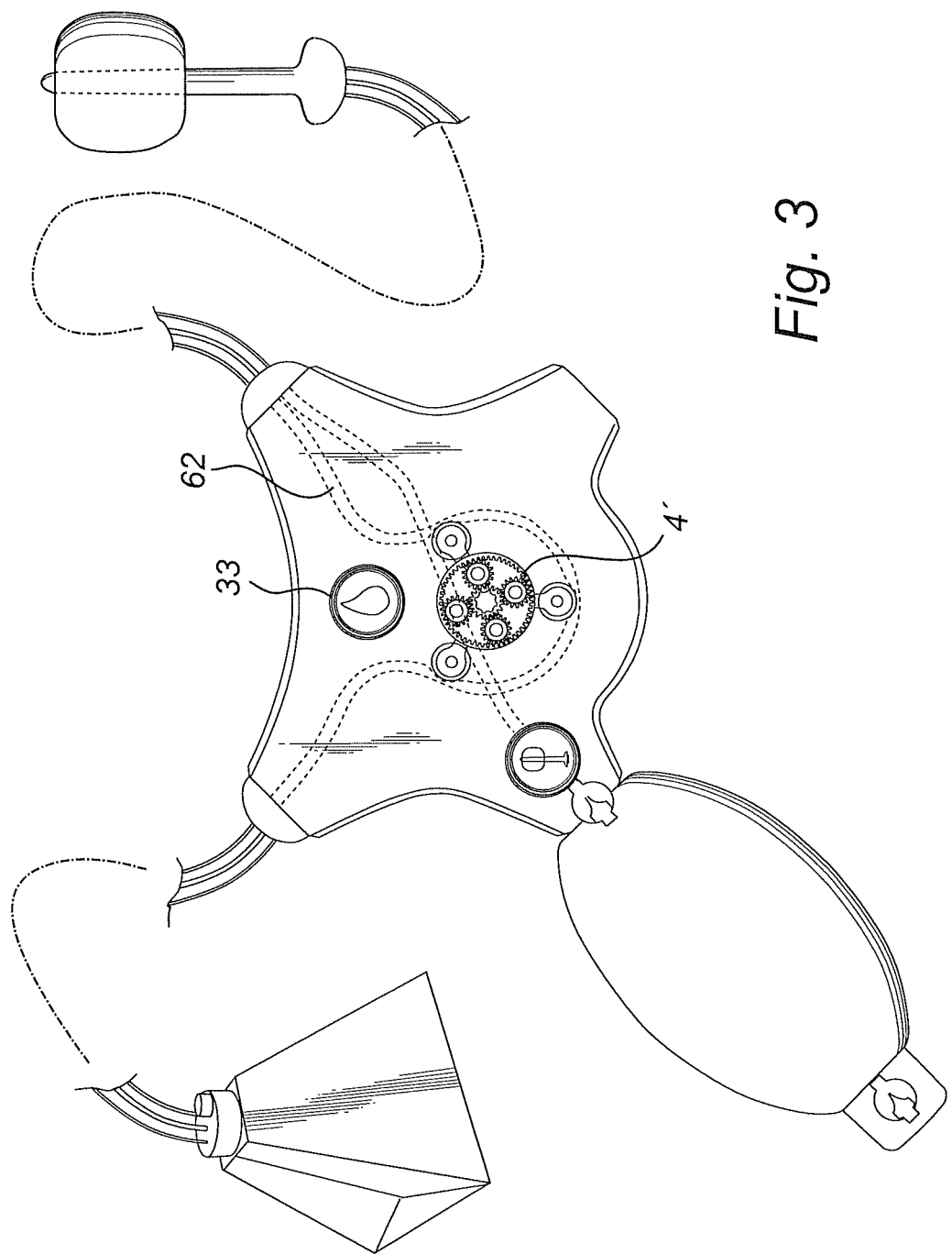
FIG. 3 is a schematic overview of an irrigation system according to a third embodiment of the invention.

The third embodiment, illustrated in FIG. 3, also resembles the above-discussed previous embodiments.

However, here the first pump 4' is a powered pump, here realized as a peristaltic pump acting directly on a tube 62' leading from the reservoir to the probe. For activation of the pump 4', a control element 33, such as a control button, is provided on the control unit, which activates the pump when depressed.

The irrigation liquid can be any liquid which is capable of irrigation the body cavity of interest. In order to stimulate bowel movements suitable irrigation liquids includes water, hypertonic aqueous salt solutions, solutions or suspensions of cathartic agents, such as bisacodyl or phenolphthalein, and mineral oil.

By use of the present invention, anal irrigation can be carried out by the following steps:

The reservoir is filled with a liquid, e.g. regular tap water,
The reservoir and the probe are connected to the control unit,
The probe is inserted into the rectum,
The second pump 5 is operated to inflate the balloon, for fixing the probe in the body,
The first pump 4 is operated to transfer irrigation liquid from the reservoir to the probe for irrigation,
When irrigation is completed, overpressure may be removed from the reservoir, and the balloon is deflated, and
The probe is removed.

The person skilled in the art realizes that the present invention is not limited to the preferred embodiment. For example many different types of hand-operated or powered pumps may be used. Further, the valves and the controls for the valves may be realized in many different ways. Also, the pumping of the irrigation liquid may be direct or indirect.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

I claim:

1. An irrigation system, comprising:
   a reservoir for an irrigation liquid;
   a probe for arrangement in a user, wherein said probe comprises an inflatable balloon for fixing the probe in a body cavity;
   a first pump configured to directly or indirectly pump the irrigation liquid from the reservoir to the probe;
   a second pump to pump a fluid to the balloon for inflation;
   a control unit to control the transfer of said irrigation liquid and said fluid, wherein said control unit further comprises a valve for releasing fluid from the balloon for deflation, said valve being provided with a manually operable balloon control element, wherein said control unit and said first and second pumps are arranged as an integrated unitary component, and wherein the control unit comprises a housing that is in direct physical contact with the first pump and the second pump; and
   tubing arranged to provide fluid communication between said reservoir and said integrated unitary component, and between said integrated unitary component and said probe;
   wherein said manually operable balloon control element is arranged in a vicinity of the second pump.

2. The irrigation system of claim 1, wherein the first pump is arranged to directly pump irrigation liquid from the reservoir to the probe.

3. The irrigation system of claim 1, wherein the first pump is arranged to pump a gas into the reservoir to create a pressure in the reservoir to displace the irrigation liquid therefrom and feed it to the probe.

4. The irrigation system of claim 1, wherein the control unit has a planar shape, with the tubing extending therethrough.

5. The irrigation system of claim 1, wherein the irrigation system is a rectal irrigation system.

6. The irrigation system of claim 1, wherein the control unit is separate from said reservoir.

7. The irrigation system of claim 1, wherein the control unit comprises at least three corners, wherein the first pump is arranged at a first corner and the second pump is arranged at a second corner.

8. The irrigation system of claim 7, wherein the control unit comprises at least four corners, wherein the tubing connecting the reservoir to the control unit is arranged at a third corner, and the tubing connecting the control unit to the probe is arranged at a. fourth corner.

9. The irrigation system of claim 1, wherein the control unit further comprises a reservoir control valve to release pressure from the reservoir, said reservoir control valve being provided with a manually operable reservoir control element.

10. The irrigation system of claim 9, wherein the manually operable reservoir control element is a control button.

11. The irrigation system of claim 9, wherein the manually operable reservoir control element is arranged in the vicinity of the first pump.

12. The irrigation system of claim 1, wherein at least one of the first and second pump is a manually operable pump.

13. The irrigation system of claim 12, wherein the manually operable pump is a bulb or a bellow pump.

14. The irrigation system of claim 12, wherein both the first and second pumps are manually operable pumps.

15. The irrigation system of claim 14, wherein the tubing comprises a first tube connecting the first pump and the reservoir, a second tube connecting the reservoir and the probe, and a third tube connecting the second pump and the probe.

16. The irrigation system of claim 14, wherein the first pump and second pump are arranged visibly discernible from each other by having at least one of different shapes and different colors.

17. The irrigation system of claim 12, wherein at least one of the first pump and second pump is a powered pump.

18. The irrigation system of claim 17, wherein the powered pump is an electrically or pneumatically operated pump.

19. The irrigation system of claim 17, wherein the control unit further comprises a pump control element for activation of the powered pump.

20. The irrigation system of claim 19, wherein the pump control element is a control button.

21. A rectal irrigation system, comprising:
a reservoir for an irrigation liquid;
a rectal catheter for arrangement in a user, wherein said rectal catheter comprises an inflatable balloon for fixing the rectal catheter in rectum;
a first pump to directly or indirectly pump the irrigation liquid from the reservoir to the rectal catheter;
a second pump to pump a fluid to the balloon for inflation;
a control unit configured to control the transfer of said irrigation liquid and said fluid, wherein said control unit comprises a valve for releasing fluid from the balloon for deflation, said valve being provided with a manually operable balloon control element and said control unit being separate from said reservoir, wherein said control unit and said first and second pumps are arranged as an integrated unitary component, the control unit comprising a housing that is in direct physical contact with the first pump and the second pump; and
tubing arranged to provide fluid communication between said reservoir and said integrated unitary component, and between said integrated unitary component and said rectal catheter;
wherein said manually operable balloon control element is arranged in a vicinity of the second pump.

22. An irrigation system, comprising: a reservoir for an irrigation liquid; a probe for arrangement in a user, wherein said probe comprises an inflatable balloon for fixing the probe in a body cavity; a first pump configured to directly or indirectly pump the irrigation liquid from the reservoir to the probe; a second pump to pump a fluid to the balloon for inflation; a control unit to control the transfer of said irrigation liquid and said fluid, wherein said control unit further comprises a valve for releasing said fluid from the balloon for deflation, said valve being provided with a manually operable balloon control element, wherein said control unit and said first and second pumps are arranged as an integrated unitary component, wherein the control unit comprises at least three corners, wherein the first pump is arranged at a first corner and the second pump is arranged at a second corner; and tubing arranged to provide fluid communication between said reservoir and said integrated unitary component, and between said integrated unitary component and said probe; wherein said manually operable balloon control element is arranged in a vicinity of the second pump.

23. The irrigation system of claim 22, wherein the control unit comprises at least four corners, wherein the tubing connecting the reservoir to the control unit is arranged at a third corner, and the tubing connecting the control unit to the probe is arranged at a fourth corner.

* * * * *